(12) United States Patent
Yang et al.

(10) Patent No.: US 11,582,971 B2
(45) Date of Patent: Feb. 21, 2023

(54) CRYSTALLINE FORMS OF DELTAMETHRIN AND METHODS OF USE THEREOF

(71) Applicant: New York University, New York, NY (US)

(72) Inventors: Jingxiang Yang, New York, NY (US); Xiaolong Zhu, New York, NY (US); Bart Kahr, Brooklyn, NY (US); Michael D. Ward, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 202 days.

(21) Appl. No.: 17/032,254

(22) Filed: Sep. 25, 2020

(65) Prior Publication Data
US 2021/0092957 A1 Apr. 1, 2021

Related U.S. Application Data

(60) Provisional application No. 62/906,346, filed on Sep. 26, 2019.

(51) Int. Cl.
| | |
|---|---|
| C07C 255/41 | (2006.01) |
| A01N 53/00 | (2006.01) |
| A01N 25/34 | (2006.01) |
| A01N 25/12 | (2006.01) |

(52) U.S. Cl.
CPC ............. *A01N 53/00* (2013.01); *A01N 25/12* (2013.01); *A01N 25/34* (2013.01); *C07C 255/41* (2013.01); *C07B 2200/13* (2013.01)

(58) Field of Classification Search
None
See application file for complete search history.

(56) References Cited

PUBLICATIONS

Owen (J. Chem. Soc. Perkin Trans. I, 1975, 0, 1865). (Year: 1975).*
Mabaso M. L. H., et al., "Historical review of malarial control in southern African with emphasis on the use of indoor residual house-spraying" Tropical Medicine and International Health, Aug. 2004, vol. 9, No. 8, pp. 846-756.
Janko M. M., et al., "Strengthening long-lansting isecticidal nets effectiveness monitoring using retrospective analysis of cross-sectional, population-based surveys across sub-Saharan Africa" Scientific Reports, (2018) 8:17110.
Casida J. E., et al., The greening of pesticide-environment interactions: some personal observations, Environmental Heath Prospectives, Apr. 2012, vol. 120, No. 4, pp. 487-493.
Elissa N. and Curtis C. F., "Evaluation of different formulations of deltamethrin in comparison with permethrin for impregnation of netting", Pestic. Sci., 1995, vol. 44, pp. 363-367.

(Continued)

*Primary Examiner* — Sudhakar Katakam
*Assistant Examiner* — Jennifer C Sawyer
(74) *Attorney, Agent, or Firm* — Troutman Pepper Hamilton Sanders LLP

(57) ABSTRACT

The present invention relates to a novel crystalline form of deltamethrin, which is a pyrethroid compound useful as a pest control agent. The present invention further relates to a process of preparing the novel crystalline form, and to methods of controlling pests using the novel crystalline form.

17 Claims, 9 Drawing Sheets

(56) References Cited

PUBLICATIONS

Casida J. E., "Michael Elliott's billion dollar crystals and other discoveries in insecticide chemistry", Pest. Manag. Sci. 2010, vol. 66, pp. 1163-1170.

Owen J. D., "Absolute configuration of the most potent isomer of the pyrethroid insecticide α-Cyano-3-phenoxybenzyl cis-3-(2,2-Dibromovinyl)-2,2-dimethylcyclopropanecarboxylate by Crystal Structure Analysis", J.C.S. Perkin I, published on Jan. 1, 1975. Downloaded by New York Unviersity on Feb. 19, 2019, pp. 1865-1868.

Saavedra-Rodriguez K., et al., "Exome-wide association of deltamethrin resistance in Aedes aegypti from Mexico" Insect. Molecular Biology, 2019, pp. 1-14.

Bellinato D. F. et al., "Resistance status to the insecticides temephos, deltamethrin, and diflubenzuron in Brazilian Aedes aegypti populations", BioMed. Research International, 2016, 12 pages.

Elliott M., et al., "Synthetic insecticide with a new order of activity", Nature, 1974, vol. 248, pp. 710-711.

Berlinger M. J., et al., "A rapid method for screening insecticides in the laboratory", Pestic. Sci. 1996, vol. 46, pp. 345-353.

Sparks T. C., "Insecticides discovery: An evalatuation and analysis", Pesticides Biochemistry and Physiology, 2013, vol. 107, pp. 8-17.

Tokponnon F. T., et al., "Implications of insecticide resistance for malaria vector control with long-lasting insecticidal nets: evidence from health facility data from Benin", Malaria Journal, 2018, vol. 18, No. 37, pp. 1-9.

Paton D. G., et al., "Exposing anopheles mosquitoes to antimalarials blocks Plasmodium parasite transmission", Nature, 2019, vol. 567, pp. 239-243.

Riveron J. M., et al., "Escalation of pyrethroid resistance in the malaria vector Anopheles funestus induces a loss of efficacy of PBO-based insecticide-treated nets in Mozambique", 2019, Published by Oxford University Press for the Infectious Diseases Society of America.

Mandeng S. E., et al., "Spatial and temporal development of deltamethrin resistance in malaria vectors of the Anopheles gambiae complex from North Cameroon", PLOS One, 2019, pp. 1-22.

Ruzo L. O., et al., Pyrethroid photochemistry: Decamethrin, J. Agric. Food Chem. 1977, vol. 25, No. 6, pp. 1385-1394.

\* cited by examiner

FIG. 1A
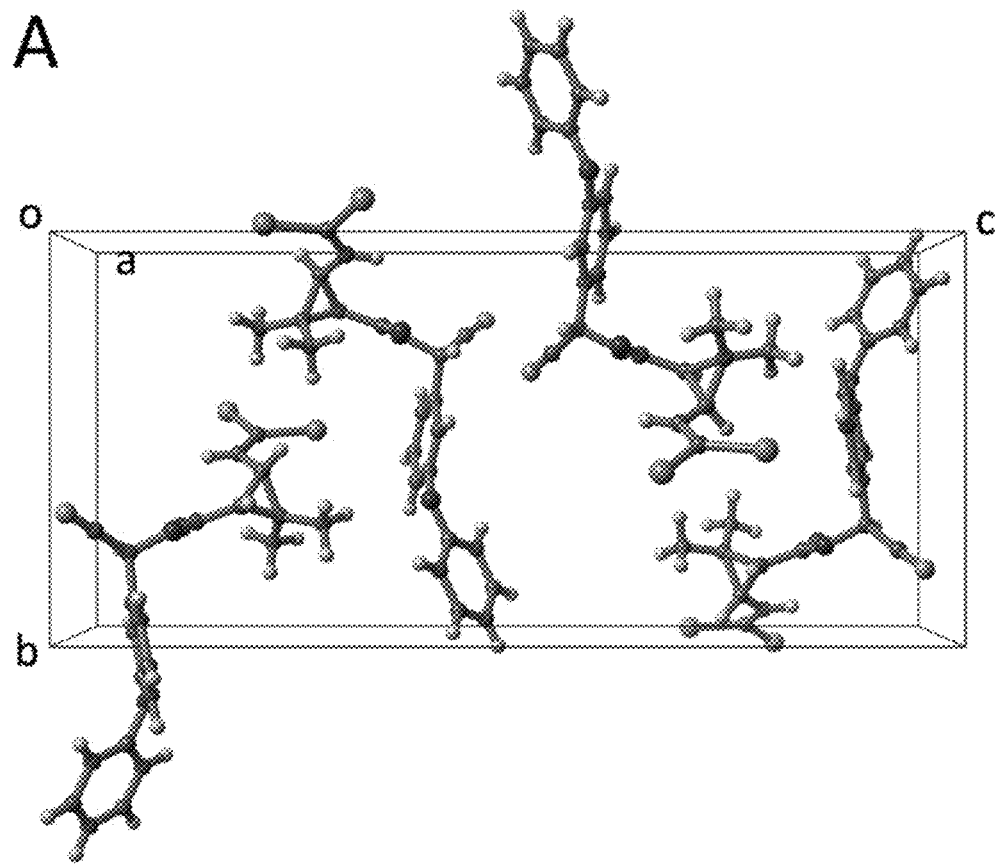
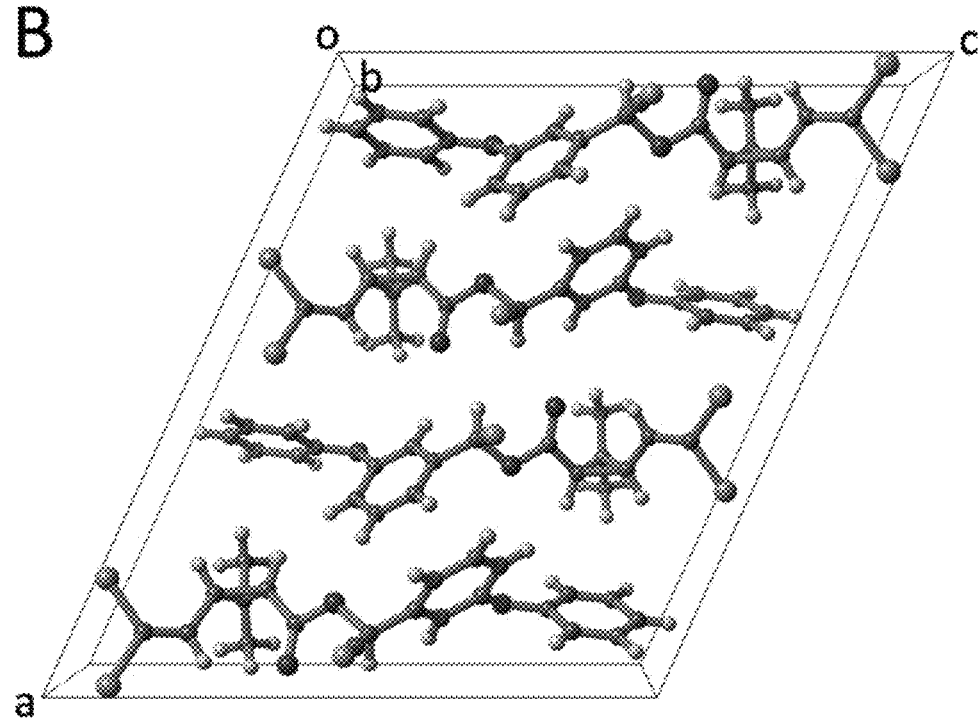
FIG. 1B

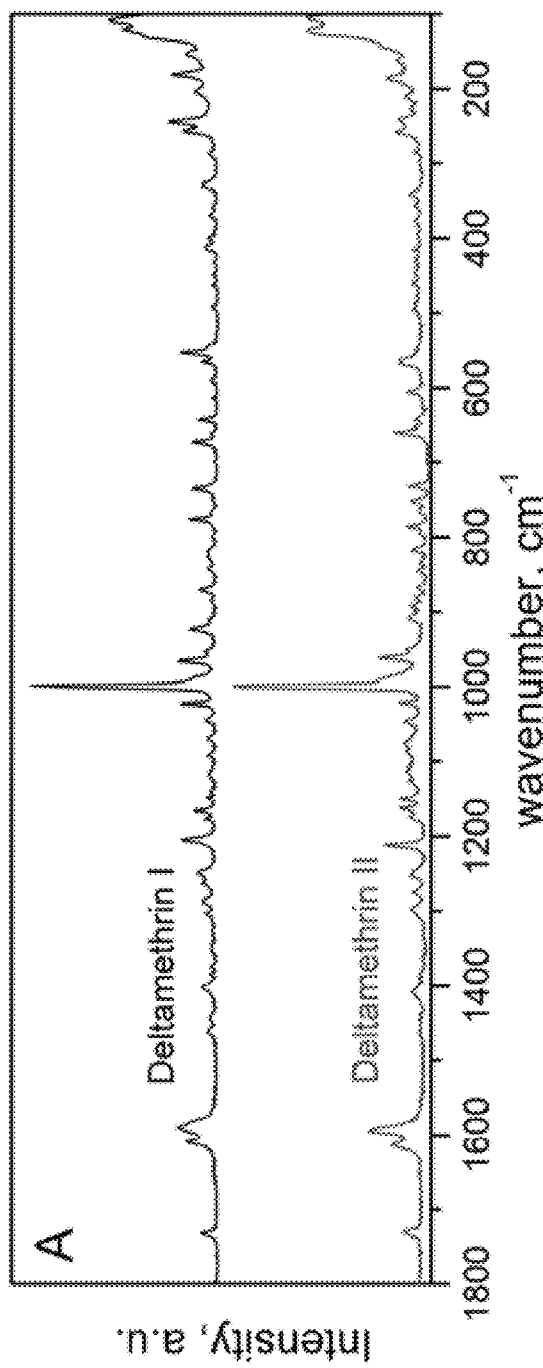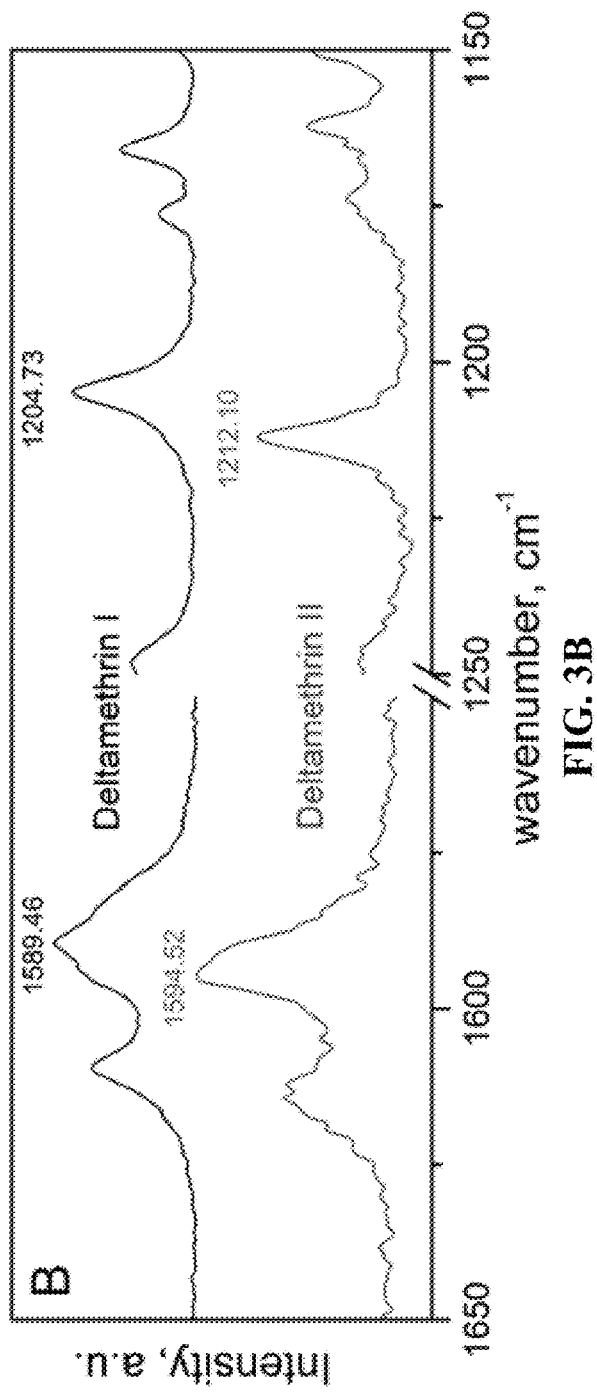

FIG. 5A
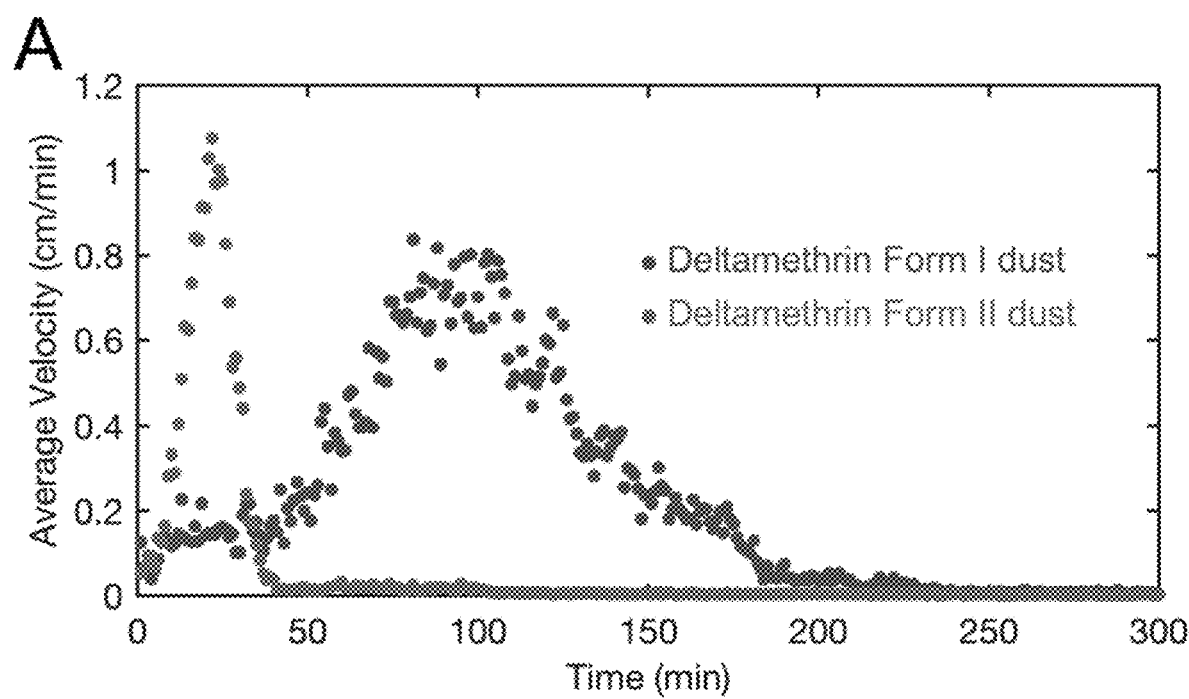
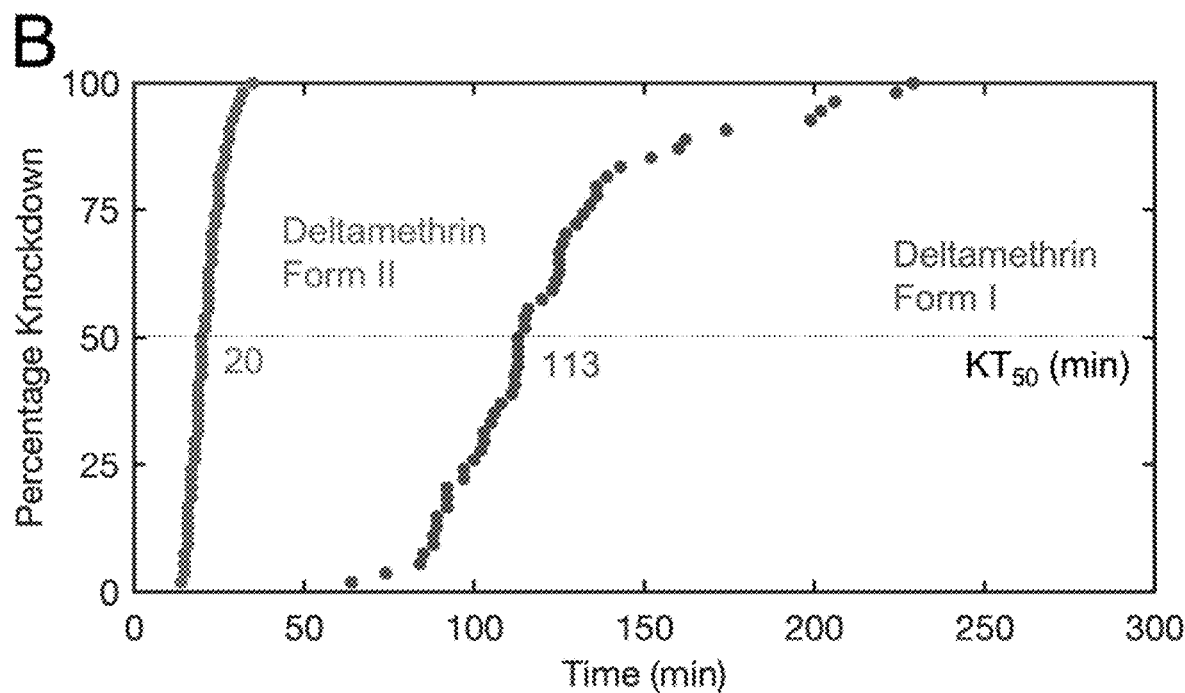
FIG. 5B

FIG. 7A
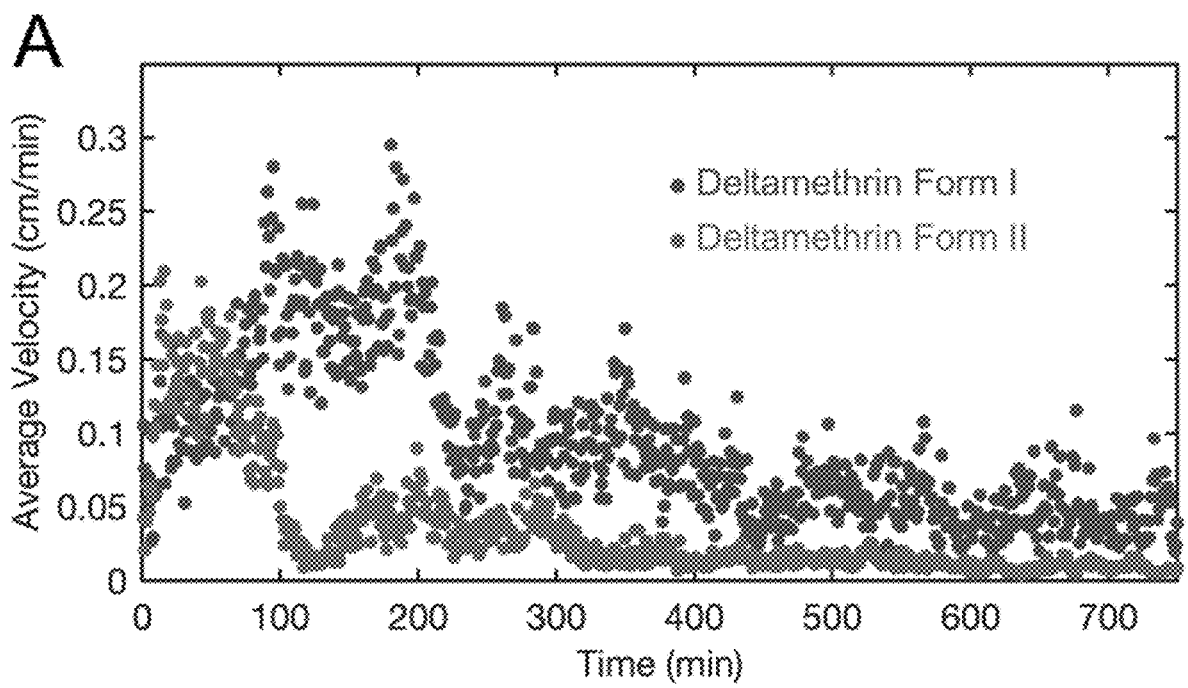
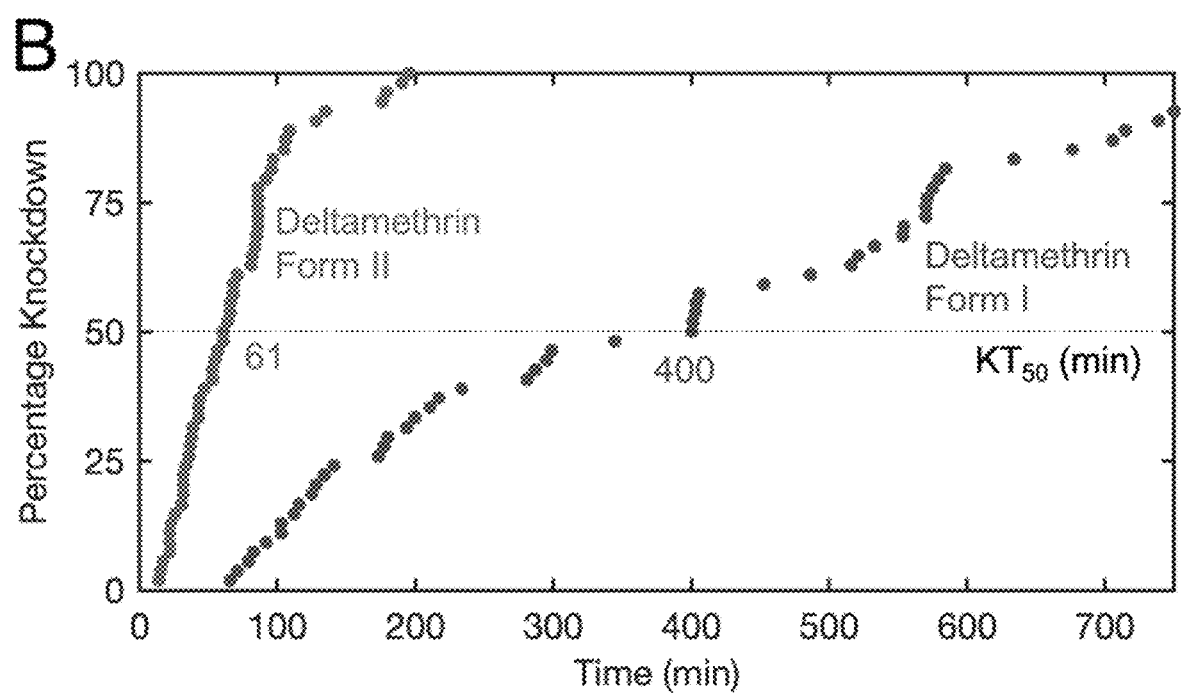
FIG. 7B

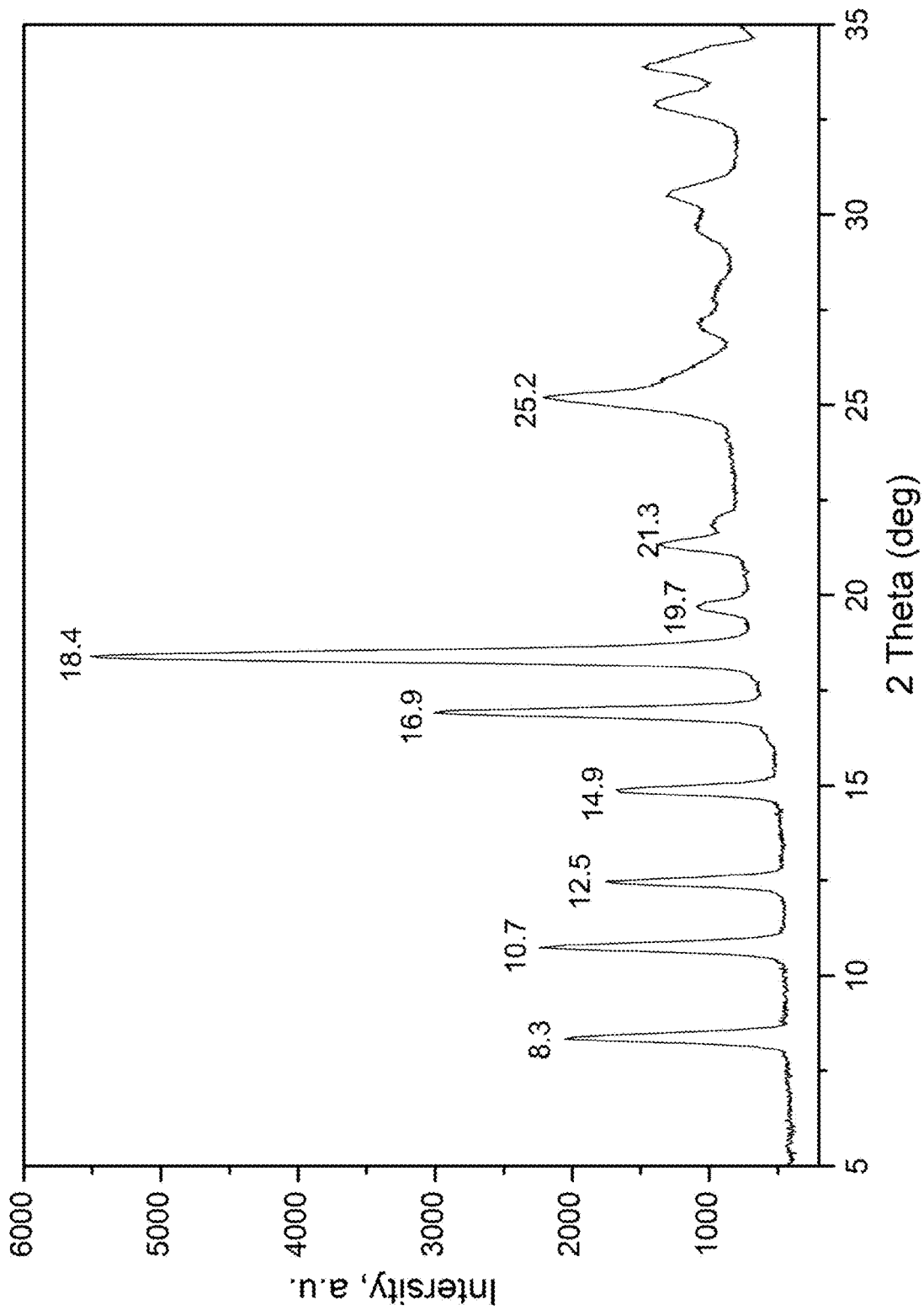

CRYSTALLINE FORMS OF DELTAMETHRIN AND METHODS OF USE THEREOF

CROSS-REFERENCE TO RELATED APPLICATIONS

This application claims priority to U.S. Provisional Patent Application No. 62/906,346, filed on Sep. 26, 2019, the contents of which is herein incorporated by reference in its entirety.

STATEMENT AS TO FEDERALLY FUNDED RESEARCH

This invention was made with Government support under grant DMR0147003 awarded by National Science Foundation. The Government has certain rights in this invention.

FIELD OF INVENTION

The present invention relates to crystalline forms of a pyrethroid compound deltamethrin, which are useful as pest control agents, and methods of preparing thereof.

BACKGROUND OF THE INVENTION

Crystallization has played a major role in the rise of deltamethrin, a pyrethroid insecticide, (S)-cyano(3-phenoxyphenyl) methyl (1R,3R)-3-(2,2-dibromovinyl)-2,2-dimethylcyclopropane-1-carboxylate, which is represented by the following Formula I

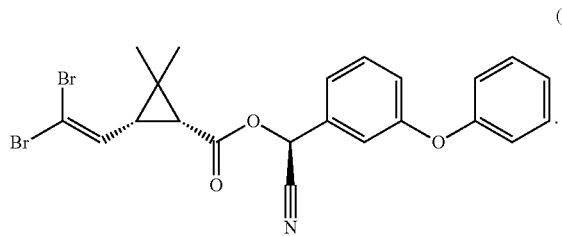

(I)

Deltamethrin has been a leading compound providing crop protection and malaria control during the past half-century. Even though deltamethrin is a comparatively complex compound, the fractional crystallization of the most potent 1R, cis, αS, stereoisomer (Formula I), followed by epimerization of the 1R, cis, αR stereoisomer, alleviated the cost of wasted byproducts and the separation of diastereoisomers. Casida, J. E. Michael Elliott's billion-dollar crystals and other discoveries in insecticide chemistry, *Pest. Manag. Sci.* 2010, 66, 1163-1170.

Despite the success of deltamethrin products, notably in long-lasting insecticidal bed nets, mosquito resistance to the pyrethroid class of insecticides, to which deltamethrin belongs, now threatens gains against malaria made during the past generation. Kleinschmidt, I.; Bradley, J.; Knox, T. B., et al. Implications of insecticide resistance for malaria vector control with long-lasting insecticidal nets: a WHO-coordinated, prospective, international, observational cohort study. *Lancet Infect Dis.* 2018, Apr. 9.

Accordingly, there is a strong, unmet need for improved pest control agents, e.g., improved pyrethroid pesticides, to help satisfy the ongoing need to counteract the significant problem of pesticide resistance.

SUMMARY OF THE INVENTION

In one aspect, the present invention provides a crystalline form of deltamethrin, which is Form II.

In one embodiment, the present invention provides the crystalline form which is Form II having a Raman spectrum substantially as shown in FIG. 8.

In another embodiment, the present invention provides the crystalline form which is Form II having a thin film X-ray diffraction pattern substantially as shown in FIG. 9.

In another embodiment, the present invention provides the crystalline form which is Form II having a thin film X-ray diffraction pattern comprising peaks at 8.3, 10.7, 16.9, 18.4, and 25.2 degrees two-theta (2θ).

In another embodiment, the present invention provides the crystalline form which is Form II having a thin film X-ray diffraction pattern comprising peaks at 8.3, 10.7, 12.5, 14.9, 16.9, 18.4, 19.7, 21.3, and 25.2 degrees two-theta (2θ).

In another embodiment, the present invention provides the crystalline form which is Form II having a single crystal structure determined at 100° K and refined in the space group C2, Z=4, a=20.753(4) Å, b=6.1857(12) Å, c=17.955(4) Å, β=114.654(3°), V=2094.81 Å.

In another embodiment, the present invention provides the crystalline form which is Form II which is substantially isolated.

In another embodiment, the present invention provides the crystalline form which is Form II which is substantially free of other crystalline forms.

In another aspect, the present invention provides a process for preparing the deltamethrin crystalline form which is Form II, comprising melting deltamethrin Form I, cooling the molten deltamethrin to room temperature, and growing crystals of deltamethrin from the molten deltamethrin.

In another aspect, the present invention provides a pesticidal composition comprising the crystalline form of deltamethrin which is Form II.

In one embodiment, the present invention provides the pesticidal composition, wherein the crystalline form is present in the composition in an amount of about 0.01% to about 5% by weight.

In one embodiment, the present invention provides the pesticidal composition, wherein the crystalline form is present in the composition in an amount of about 0.5% by weight.

In yet another aspect, the present invention provides a method of controlling a pest comprising applying to the pest or its locus the crystalline form as described above or the pesticidal composition as described above.

In one embodiment, the pest is an insect.

In one embodiment, the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, green-striped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, red-humped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellow-necked caterpillar, wasps, and webworms.

BRIEF DESCRIPTION OF THE DRAWINGS

FIGS. 1A-1B depict the single crystal structure of deltamethrin Form I (FIG. 1A) and deltamethrin Form II (FIG. 1B).

FIGS. 3A-3B depict Raman spectra of deltamethrin Form I and Form II. FIG. 3A shows Raman spectra of Form I (black) and Form II (red) collected from deltamethrin single crystals. The size of the laser beam was 0.7 μm. FIG. 3B shows the expanded region of the Raman spectrum revealing the most substantial differences between the two polymorphs.

FIGS. 5A-5B show graphs comparing lethality of the two crystalline forms of deltamethrin. FIG. 5A is a graph depicting the velocities of fruit flies exposed to deltamethrin Form I and II dusts; FIG. 5B is a graph of the comparison of *Drosophila melanogaster* knockdown times in 2 mg of dusts containing deltamethrin Form I (0.05%) and deltamethrin Form II obtained from Form I dust by heating. The corresponding average knockdown times and median knockdown times (KT50) are denoted.

FIGS. 6A-6B show graphs comparing lethality of the two crystalline forms of deltamethrin. FIG. 6A is a graph depicting the velocities of mosquitos exposed to deltamethrin Form I and II dusts; FIG. 6B is a graph of the comparison of *Aedes aegypti* mosquitos knockdown times in 2 mg of dusts containing deltamethrin Form I (0.05%) and deltamethrin Form II obtained from Form I dust by heating. The corresponding average knockdown times and median knock-down times (KT50) are denoted.

FIGS. 7A-7B are a lethality comparison of the two forms of deltamethrin. FIG. 7A is a graph depicting the velocities of fruit flies exposed to crystalline films (2.2*2.2 cm$^2$) of deltamethrin Form I and II; FIG. 7B is a comparison of *Drosophila melanogaster* knockdown times on crystalline films (2.2*2.2 cm$^2$) of deltamethrin Form I and Form II.

FIG. 9 is a thin film XRD spectrum of deltamethrin Form II with labeled prominent peaks.

DETAILED DESCRIPTION

Figures 2A, 2B:
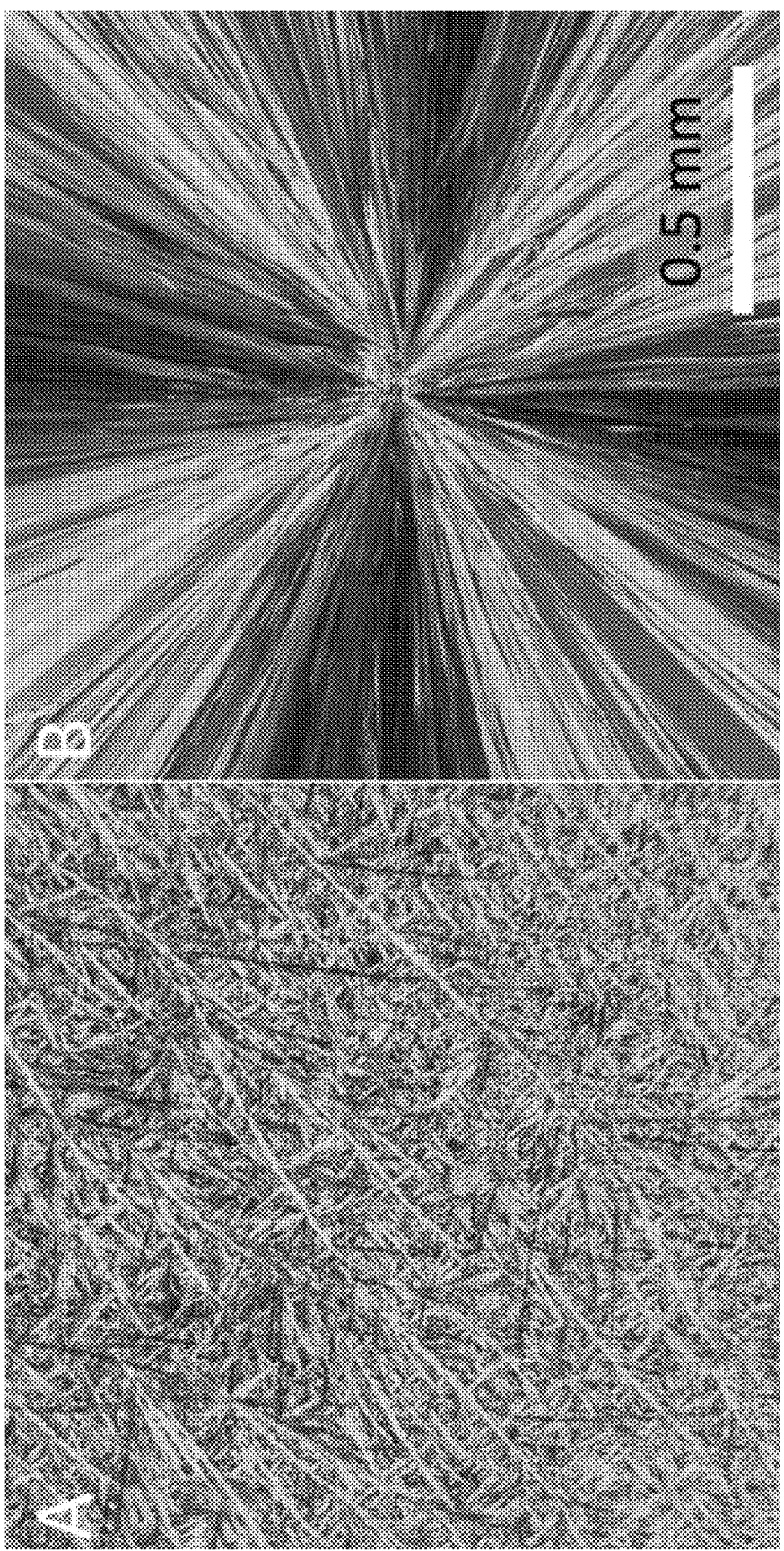
FIGS. 2A-2B show how growth from melt at room temperature produces two distinct polycrystalline textures assigned to deltamethrin Form I (FIG. 2A) and deltamethrin Form II (FIG. 2B). Crystalline thin film of deltamethrin was observed between crossed polarizers.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

A "pest", as used herein, refers to not only insects, but also is a generic term for small animals that may directly or indirectly damage, and thereby affect, humans, produce, machines, equipment, and so on, by colonizing, attacking, irritating, or feeding upon them, or competing for host nutrients. Examples of pests include mosquitos, flies, ants, spiders, centipedes, cockroaches, geckos, mice, pigeons, crows, and any other similar animals.

As used herein the term "to control a pest" means to expel, kill, destroy, or exterminate pests, prevent or mitigate proliferation of pests, protect targets from pests, and control (or inhibit) the growth of pests. Controlling pests includes enticing pests in order to exert the pest control effects described above.

As used herein the term "pesticidal composition" refers to a composition comprising a substance or mixture of substances capable of expelling, killing, destroying, exterminating, preventing, or mitigating any pest.

As used herein the term "effective" applied to dose or amount refers to that quantity of a pesticide that is sufficient to result in a desired pesticidal action or activity.

Typically, different crystalline forms of the same substance have different bulk properties relating to, for example, hygroscopicity, solubility, stability, and the like. Forms with high melting points often have good thermodynamic stability which is advantageous in prolonging shelf-life of formulations containing the solid form. Forms with lower melting points often are less thermodynamically stable, but are advantageous in that they have increased water solubility, translating to increased drug bioavailability. Forms that are weakly or non-hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder or thin film diffraction (XRD). Other characterization methods such as Raman spectroscopy, differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms are most commonly characterized by XRD. An XRD pattern of reflections (peaks) is typically considered a fingerprint of a particular crystalline form. It is well known that the relative intensities of the XRD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRD herein is meant to encompass the above-mentioned variations.

In the same way, temperature readings in connection with melting point, DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

In some embodiments, the crystalline form of deltamethrin is anhydrous and non-solvated. By "anhydrous" is meant that the crystalline form of deltamethrin contains essentially no bound water in the crystal lattice structure, i.e., the compound does not form a crystalline hydrate.

In some embodiments, the crystalline form of the invention is substantially isolated. By "substantially isolated" is meant that a particular crystalline form of deltamethrin is at least partially isolated from impurities. For example, in some embodiments a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of deltamethrin is substantially free of other crystalline forms. The phrase "substantially free of other crystalline forms" means that a particular crystalline form of deltamethrin comprises greater than about 80%, greater than about 90%, greater than about 95%, greater than about 98%, greater than about 99% or greater than about 99.5% by weight of the particular crystalline form.

Despite the widespread study and application of deltamethrin, only one crystal structure has been reported in the Cambridge Structural Database, which has been designated herein as Form I (CSD refcode: PXBVCP10). See Owen, J. Absolute configuration of the most potent isomer of the pyrethroid insecticide α-cyano-3-phenoxybenzyl cis-3-(2,2-dibromovinyl)-2,2-dimethylcyclopropanecarboxylate by crystal structure analysis. *J. Chem. Soc., Perkin Trans.* 1, 1975, 0, 1865-1868, which has been incorporated by reference herein in its entirety.

The crystal structure of Form I has been redetermined at 100° K ($P2_12_12_1$, Z=4, a=6.1437(8) Å, b=12.2386(15) Å, c=26.935(3) Å, V=2025.25 Å$^3$, FIG. 1A).

It has been surprisingly discovered by the present inventors that cooling of molten deltamethrin when confined between glass slides generates a supercooled melt that can be stable for days at room temperature. It has been further surprisingly discovered that growth from the melt at room temperature produces fine spherulites (FIG. 2B) and sometimes fields of chaotic polycrystalline textures (FIG. 2A).

Micro-Raman spectroscopy reveals that chaotic textures corresponded to the known deltamethrin Form I (FIG. 2A), whereas the spherulites represent a novel, previously unknown polymorph, hereby designated as Form II (FIG. 2B).

When Form II is allowed to grow at 50° C., individual crystals large enough for X-ray analysis can be harvested from the melt. The single crystal structure of Form II has been determined at 100 K and refined in the space group C2, Z=4, a=20.753(4) Å, b=6.1857(12) Å, c=17.955(4) Å, β=114.654(3°), V=2094.81 Å$^3$ (FIG. 1B).

Compositions and Methods of Pest Control

Deltamethrin Form II, and compositions comprising deltamethrin Form II, may be used as agents to control pests, i.e. as pesticides and/or pest repellents.

Some embodiments of using deltamethrin Form II and compositions comprising deltamethrin Form II cover a range of applications involving humans, non-human animals (including domesticated companion animals, livestock, and wildlife), and plants, including recreational, veterinary, agricultural, silvicultural, horticultural, and environmental applications. Other embodiments encompass disease control applications, such as controlling the spread of disease among animals and/or plants by controlling the vector for that disease. Exemplary vector-borne diseases of humans and non-human animals include, but are not limited to: Lyme disease; Dengue Fever; Yellow Fever; tick-borne babesiosis; tuleremia; powassan-like virus infection; tick-borne encephalitis; relapsing fever; malaria; encephalitis, such as the disease caused by the West Nile Virus, Eastern equine encephalitis, St. Louis encephalitis, Venezuelan equine encephalitis, Western equine encephalitis and Lacrosse encephalitis; Colorado Tick Fever; ehrlichiosis; Rocky Mountain Spotted Fever; and the Plague. Exemplary, non-limiting vector-borne diseases of plants are Dutch Elm disease, elm yellows phytoplasmas, and apply powdery mildew. Some disclosed pest control compositions may offer certain advantages, such as long term effect due to extended residual action, or high levels of safety and efficacy for veterinary, agricultural, and nuisance pest applications.

In any particular embodiment, a composition is administered in an effective amount. That amount may depend on a variety of factors, including (but not limited to) the area to be treated, the pest to be treated, its metabolism, its behavior (e.g., feeding habits, breeding, daily or seasonal activity cycles, development, nesting habits, etc.), and behavior of the host the pest infests.

In some embodiments, deltamethrin Form II and/or a composition comprising deltamethrin Form II is applied once, while alternative embodiments employ plural applications of the same composition or different compounds or compositions. In particular embodiments, a composition is administered on an hourly, daily, weekly, monthly, quarterly, or annual basis. In any particular embodiment, the frequency of application may be regular or irregular, and the time elapsed between successive applications may be the same or different. For example, and without limitation, deltamethrin Form II and/or a composition comprising deltamethrin Form II may be applied every eight to twelve hours; four times per day at irregular intervals; every evening; four times per week; every other day; every other week; every other month; twice a month; every three months; every six months; every nine months; or annually. Like the amount of the compound or composition used in an embodiment, the frequency and number of applications of that compound or composition may depend on a variety of factors, including (but not limited to) the area to be treated, the pest to be treated, its metabolism, and its behavior (e.g., feeding habits, breeding, daily or seasonal activity cycles, development, nesting habits, etc.), and behavior of the host the pest infests.

Included are embodiments where deltamethrin Form II and/or a composition comprising deltamethrin Form II is applied to a particular human, non-human animal, plant, inanimate object, or environmental locus. Deltamethrin Form II and/or a composition comprising deltamethrin Form II may be applied directly to the pest, thus causing the pest to directly contact the composition, or may be applied to some locus or host that is expected to come into contact with the pest.

If applied to a locus, deltamethrin Form II and/or a composition comprising deltamethrin Form II may be applied to the locus generally, such as by an aerosol or fumigant, or applied to a human, non-human animal, plant, or inanimate object within that locus. The size of a particular locus may vary considerably according to the method of application. For example, in area-wide applications, deltamethrin Form II and/or a composition comprising deltamethrin Form II is dispersed over a locus of an environment, rather than intentionally directed at a particular pest, human, plant, or inanimate object. The locus of an area-wide application may be several hundred to thousands of acres, if deltamethrin Form II and/or a composition comprising deltamethrin Form II is used for agricultural spraying or to control the spread of a vector-borne disease; in structural applications, such as controlling pests within a home or restaurant, the locus may be several hundred several thousand square feet. However, in personal, veterinary, or horticultural applications, such as using topical pest repellent spray or ointment, or using a flea shampoo to bathe a pet, the locus may be limited to the area in the immediate vicinity of the animal, plant, or human host.

The size of the locus also may vary according to such factors as the intended application, presence of humans or non-human animals, level of human or non-human activity within the locus, type of formulation embodying deltamethrin Form II and/or a composition comprising deltamethrin Form II, and environmental factors, such as wind speed, humidity, temperature, and anticipated rainfall.

Methods of application include dusting, spraying, atomizing, immersing, coating, dressing, scattering, and pouring. A particular method of application may be selected in accordance with the intended objectives of and circumstances related to a particular use.

The frequency of application also may depend on the residual action of deltamethrin Form II. "Residual action" refers to the length of time a compound or composition may exist in a particular environment and remain effective.

Deltamethrin Form II and/or the compositions comprising deltamethrin Form II described herein may be employed in formulations intended for use in public or private homes, residences, businesses, restaurants, hospitals, or other similar places of human activity. In such embodiments, the formulations may be used to kill or repel pests, such as mosquitoes, ants, spiders, or roaches, and may be applied directly to the pests or a locus the pest is expected to contact. For example, flea bomb or other fumigant containing deltamethrin Form II as an active ingredient could be used within a home (such as applied within a particular room of a home to control fleas). As another example, a commercial spray containing deltamethrin Form II as an active ingredient could be applied to the floors and other interior spaces of a restaurant to control cockroaches. In any such embodiment, the formulation may kill or repel a pest by directly contacting the pest, may be induced into the atmosphere of the locus, or may be applied to a human, non-human animal, plant, or inanimate object (e.g., the surface of a floor) expected to come into contact with the pest.

Certain embodiments employ formulations for use on humans, non-human animals, or plants for their protection. For example, certain formulations may be insecticides and/or acaricides sprayed onto the leaves of indoor plants for controlling aphids. Other formulations may include lotions or oils that repel pests.

Certain embodiments encompass protection of homes, buildings, or other structures from nuisance insects, such as termites, cockroaches, and/or ants. In such methods, deltamethrin Form II and/or a composition comprising deltamethrin Form II may be applied to a locus within or outside the structure protected, such as spraying onto floors or inside cupboards, or soaking the ground outside the structure. Additionally, deltamethrin Form II and/or a composition comprising deltamethrin Form II may be embedded within materials used to construct the structure, such as siding, wall studs, or beams.

Certain nontoxic compositions comprising deltamethrin Form II may be used to control pests parasitic to a particular subject. The subject may be a human or non-human animal, including domesticated animals and livestock, such as dogs, cats, birds, reptiles, cattle, swine, sheep, fowl, and goats. In such embodiments, the composition may be provided to the human or non-human animal as a topical formulation (such as a cream, lotion, ointment, dip, shampoo, spotting liquid or spray), provided in the form of a wearable product (such as a collar, ear tag, or piece of clothing), or be embedded or incorporated into items commonly used by the animal (such as, household items, like bed nets, bedding, and/or furniture).

In certain embodiments, deltamethrin Form II and/or a composition comprising deltamethrin Form II is applied in an area-wide manner, such as in protection of agricultural crops. In addition to agricultural applications, area-wide applications may include silvicultural, horticultural, or other forms of environmental pest management and control. In such embodiments, deltamethrin Form II and/or a composition comprising deltamethrin Form II may be applied to plant foliage, such as spraying or dusting, or applied to the soil, such as drenching a particular locus with a liquid formulation or applying the active ingredient in solid form to a locus. In some instances, plants within or adjacent to the locus of application may absorb deltamethrin Form II and/or a composition comprising deltamethrin Form II through their roots. In other instances, deltamethrin Form II and/or a composition comprising deltamethrin Form II will remain in the environment, such as when a composition is applied to a stagnant body of water to control mosquito larvae.

Certain embodiments use deltamethrin Form II and/or a composition comprising deltamethrin Form II described herein for pest control in food production and storage. For example, deltamethrin Form II and/or a composition comprising deltamethrin Form II may be used as an agricultural pesticide to control pests and protect grain, vegetable, herb, spice, or fruit crops. Deltamethrin Form II and/or a composition comprising deltamethrin Form II also may be used to control pests affecting other plants useful or important in agricultural or horticultural production, such as those plants or crops producing cotton, flax, tobacco, hemp, rubber, nuts, nursery stock, and ornamental plant parts.

Disclosed pest control compositions comprising deltamethrin Form II may be used to protect plant products not only during growth and production, but also during storage or transport of such products. For example, some embodiments use compositions comprising deltamethrin Form II to protect grain stored in silos, bales of cotton or tobacco stored in warehouses, or bushels of fruit being transported from an orchard.

Deltamethrin Form II and/or a composition comprising deltamethrin Form II also may be used to protect plant propagation material, such as seeds, fruit, tubers, or plant cuttings. The propagation material may be treated with the formulation before planting, such as soaking, coating, or dressing seeds prior to sowing. Compositions also may be applied to the soil where the propagation material will be planted, such as in-furrow application to protect seeds.

In such applications, deltamethrin Form II and/or a composition comprising deltamethrin Form II may be applied to provide a certain concentration of an active ingredient of the composition (i.e., deltamethrin Form II) in the environment at a particular locus. That certain concentration may be measured, established, or determined according to the needs of the user. For example, when applying a composition to crops, the rate of application may depend on the nature of soil, the type of application (e.g., spraying crop foliage, burial in soil), the crop plant to be protected, the pest to be controlled, the prevailing climatic conditions, growing season, proximity to residential areas or protected environments, and other factors. As another example, when applying a pest control composition to stored or transported agricultural products, the rate of application may depend on the localized environment (e.g., storage within a warehouse, storage under a covered shelter, transport within a trailer), expected duration of storage, product to be protected, the pest to be controlled, economic considerations, and other factors. In certain embodiments, the rates of concentration are in the range from about 0.01 to about 1000 ppm (parts-per-million), such as from about 0.1 to about 500 ppm of each active ingredient. In area-wide applications, rates of application per hectare may be from about 0.5 g/ha to 2000 g/ha, such as particularly from about 10 to 1000 g/ha, or from about 20 to 600 g/ha. As one non-limiting example, pesticides for the control of mosquito vectors of malaria may be used in area-wide applications at a rate of application of about 70 g/ha to about 1.15 kg/ha.

Use of pesticides is regulated in the United States by state and federal agencies, including the Environmental Protection Agency (EPA) and Food and Drug Administration (FDA). Relevant regulatory programs include the Federal Insecticide, Fungicide and Rodenticide Act (FIFRA) and the Federal Food, Drug and Cosmetic Act (FD&C Act). Certain articles of manufacture in accordance with these governmental and regulatory considerations may be made using disclosed pest control compositions comprising deltamethrin Form II.

In such embodiments, a pest control composition comprising deltamethrin Form II is embodied in an acceptable carrier and stored within a container capable of storing the composition for its shelf life. The container may be made of any suitable material such as plastic or other polymer, glass, metal, or the like. Printed instructions and/or a printed label indicating that the composition may be used to control pests are associated with this container. The instructions and/or label may provide information regarding the use of the composition for pesticidal purposes in accordance with the treatment method set forth herein and may be associated with the container by being adhered to the container, or accompanying the container in a package. The label may indicate the composition is approved for use as a pesticide, and the instructions may specify the pests intended to be controlled by the composition, the method and rate of application, dilution protocols, use precautions, and the like. Additionally, the container may include a feature or device for applying the composition to the pest population or locus to be treated. For example, if the article of manufacture includes a liquid composition, the feature or device may be a hand-operated, motorized, or pressurized pressure-driven sprayer. In certain embodiments, the article of manufacture includes, packaged together, a vessel-such as a tube, barrel, bottle, bottle, or can containing the composition and instructions for use of the composition for controlling a pest. In other embodiments, the article of manufacture is a device that includes the compound as part of the device, such as a surface coated with the compound, for example a bait trap or flea collar. In alternative embodiments, the article of manufacture includes packaging material containing the composition. Additionally, the packaging material may include a label indicating that the composition may be used for controlling a pest and, in particular embodiments, a pesticide for killing a pest. Examples of articles of manufacture include, but are not limited to, spray bottles of a ready-to-use formulation for household use; bottles, cans, or barrels containing concentrated formulations that may be diluted for area-wide applications; containers of concentrated formulations for use in industrial settings; flea collars or ear tags for domesticated companion animals and livestock; bottles or kits for shampooing, dipping, or cleaning domesticated companion animals or livestock; a bottle containing a formulation for human use as a shampoo or body wash; plastic tubules containing a topical oil for applying to a domesticated animal; and rodent bait boxes or host targeted bait boxes containing a pesticidal composition for killing ectoparisites infesting the host animal.

Deltamethrin Form II and/or a composition comprising deltamethrin Form II may be effective to control a pest. Exemplary pests include, without limitation, the following pests described according to taxonomic designation and/or vernacular name:

Order Acarina, including *Acarus siro, Aceria sheldoni, Aculus schlechtendali, Amblyomma* species, *Argas* species, *Boophilus* species, *Brevipalpus* species, *Bryobia praetiosa, Calipitrimerus* species, *Chorioptes* species, *Dermanyssus gallinae, Eotetranychus carpini, Eriophyes* species, *Hyalomma* species, *Ixodes* species, *Olygonychus pratensis, Ornithodoros* species, *Panonychus* species, *Phyllocoptrum*

*oleivora, Polyphagotarsonemus latus, Psoroptes* species, *Rhipicephalus* species, *Rhizoglyphus* species, *Sarcoptes* species, *Tarsonemus* species, *Tetranychus* species, *Dermacentor* species, *Aponomma* species, and *Haemaphysalis* species.

Order Homoptera, including *Aleurothrixus floccosus, Aleyrodes brassicae, Aonidiella* species, *Aphididae* species, *Aphis* species, *Aspidiotus* species, *Bemisia tabaci, Ceroplaster* species, *Chrysomphalus aonidium, Chrysomphalus dictyospermi, Coccus hesperidum, Empoasca* species, *Eriosoma lanigerum, Erythroneura* spp, *Gascardia* species, *Laodelphax* species, *Lecanium corni, Lepidosaphes* species, *Macrosiphus* species, *Myzus* species, *Nephotettix* species, *Nilaparvata* species, *Paratoria* species, *Pemphigus* species, *Planococcus* species, *Pseudaulacaspis* species, *Pseudococcus* species, *Psylia* species, *Pulvinaria aethiopica, Quadraspidiotus* species, *Rhopalosiphum* species, *Saissetia* species, *Scaphoideus* species, *Schizaphis* species, *Sitobion* species, *Trialeurodes vaporariorum, Trioza erytreae, Unaspis citri*; and *Homalodisca coagulata;*

Order Hymenoptera, including Family Formicidae, Family Apidae, and Family Bombidae, such as *Acromyrmex* species, *Atta* species, *Cephus* species, *Diprion* species, *Diprionidae* species, *Gilpinia polytoma, Hoplocampa* species, *Lasius* species, *Monomorium pharaonis, Neodiprion* species, *Solenopsis* species, and *Vespa* species;

Order Diptera, including Family Culicidae, Family Simulidae, Family Psychodidae, Family Ceratopogonidae, Family Sarcophagidae, Family Streblidae, and Family Nycteriblidae, such as *Aedes* species, *Antherigona soccata, Bibio hortulanus, Calliphora erythrocephala, Ceratitis* species, *Chrysomyia* species, *Culex* species, *Culex p. pipiens, Cuterebra* species, *Dacus* species, *Drosophila* species, *Fannia* species, *Gastrophilus* species, *Glossina* species, *Hypoderma* species, *Hyppobosca* species, *Liriomyza* species, *Lucilia* species, *Melanagromyza* species, *Musca* species, *Oestrus* species, *Orseolia* species, *Oscinellafrit, Pegomyia hyoscyami, Phorbia* species, *Rhagoletis pomonella, Sciara* species, *Stomoxys* species, *Tabanus* species, *Tannia* species, and *Tipula* species;

Order Siphonaptera, including *Ceratophyllus* species, *Xenopsylla cheopis* and other *Xenopsylla* species, *Ctenocephalides* species, *Oropsylla* species, *Pulex* species, *Opisocrostis* species, *Echidnopaga* species, and *Diamanus* species.

Order Thysanura, including *Lepisma saccharina;*

Order Lepidoptera; including *Acleris* species, *Adoxophyes* species, *Aegeria* species, *Agrotis* species, *Alabama argulaceae, Amylois* species, *Anticarsia gemmatalis, Archips* species, *Argyrotaenia* species, *Autographa* species, *Busseola fusca, Cadra cautella, Carposina nipponensis, Chilo* species, *Choristoneura* species, *Clysia ambigueua, Cnaphalocrocis* species, *Cnephasia* species, *Cochylis* species, *Coleophora* species, *Crocidolomia binotaus, Cryptophlebia leucotreta, Cydia* species, *Diatraea* species, *Diparopsis castanea, Earias* species, *Ephestia* species, *Eucosma* species, *Eupoecilia ambiguena, Euproctis* species, *Euxoa* species, *Grapholita* species, *Hedya nubiferana, Heliothis* species, *Hellula andalis, Hyphantria cunea, Keiferia lycopersicella, Leucoptera scitella, Lithocllethis* species, *Lobesia botrana, Lymantria* species, *Lyonetia* species, *Malacosoma* species, *Mamestra brassicae, Manduca sexta, Operophtera* species, *Ostrinia nubilalis, Pammene* species, *Pandemis* species, *Panolis flammea, Pectinophora gossypieua, Phthorimaea operculeua, Pieris rapae, Pieris* species, *Plutella xylostella, Prays* species, *Scirpophaga* species, *Sesamia* species, *Sparganothis* species, *Spodoptera* species, *Synanthedon* species, *Thaumetopoea* species, *Tortrix* species, *Trichoplusia ni*, and *Yponomeuta* species;

Order Coleoptera, including *Agriotes* species, *Anthonomus* species, *Atomaria linearis, Chaetocnema tibialis, Cosmopolites* species, *Curculio* species, *Dermestes* species, *Diabrotica* species, *Epilachna* species, *Eremnus* species, *Leptinotarsa decemlineata, Lissorhoptrus* species, *Melolontha* species, *Oryzaephilus* species, *Otiorhynchus* species, *Phlyctinus* species, *Popillia* species, *Psylliodes* species, *Rhizopertha* species, *Scarabeidae, Sitophilus* species, *Sitotroga* species, *Tenebrio* species, *Tribolium* species, and *Trogoderma* species;

Order Orthoptera, including *Blatta* species, *Blattella* species, *Gryllotalpa* species, *Leucophaea maderae, Locusta* species, *Periplaneta* species, and *Schistocerca* species Order Isoptera, including *Reticulitermes* species;

Order Psocoptera, including *Liposcelis* species;

Order Anoplura, including *Haematopinus* species, *Phthirus pubis* and other *Phthirus* species, *Linognathus* species, *Pediculus* species, *Pemphigus* species, and *Phylloxera* species;

Order Mallophaga, including *Damalinea* species and *Trichodectes* species;

Order Thysanoptera, including *Frankliniella* species, *Hercinothrips* species, *Taeniothrips* species, *Thrips palmi, Thrips tabaci* and *Scirtothrips aurantii* and Order Heteroptera, including *Cimex* species, *Distantiella theobroma, Dysdercus* species, *Euchistus* species, *Eurygaster* species, *Leptocorisa* species, *Nezara* species, *Piesma* species, *Rhodnius* species, *Sahlbergella singularis, Scotinophara* species and *Triatoma* species.

Order Scopriones, including *Centruriodes* species, *Euscorpius* species, *Parabuthus* species, and *Vaejovis* species.

Order Araneae, including *Latrodectus* species, *Loxosceles* species, and *Brachypelma* species.

Order Hemiptera, including *Cimicidae* species, *Enicocephalidae* species, *Pentatomidae* species, *Gerridae* species, *Saldidae* species, *Belostomatidae* species, and *Nepidae* species.

Class Diplipoda (millipedes).

Class Chilopoda (centipedes).

In particular embodiments, the pest is a member of the taxonomic order or subclass Acarina, including soft and hard ticks; Diptera, including *Tabanidae*, anophelines, and culecines; or Siphonoptera. In other particular embodiments, the pest belongs to a particular species, such as *Ixodes scapularis* (deer tick), *Aedes aegypti* (mosquito), *Xenopsylla cheopis* (rat flea), *Homalodisca coagulata* (glassy-winged sharpshooter), or *Culexpipiens* (mosquito).

Other exemplary arthropod pests and/or parasites include fleas; mosquitoes; bees, yellow jackets, and wasps; cockroaches, including the American and German cockroach; termites; houseflies and silverleaf whiteflies; lacey-winged sharpshooters or glassy-winged sharpshooters; leaf hoppers, such as the grape or potato leafhoppers; cabbage looper (Lepidoptera); ants, such as the pharaoh ant, argentine ant, carpenter ant, and fire ant; stink or lygus bugs; leafminers; western flower thrips; aphids, such as melon aphids and black bean aphids; arachnids, such as spiders, ticks, and plant mites, including two-spotted spider mites, McDaniel mites, Pacific mites, and European mites.

In one embodiment, the pest is an insect selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, webworms

EXAMPLES

The following examples illustrate specific aspects of the instant description. The examples should not be construed as limiting, as the examples merely provide specific understanding and practice of the embodiments and their various aspects.

Materials and Methods. Deltamethrin Form I powder was obtained from Sigma-Aldrich and used as supplied. Deltamethrin should be treated as a hazardous compound, may be toxic if swallowed, inhaled or brought in contact with skin. All safety conditions should be read and understood before handling.

Figure 8:
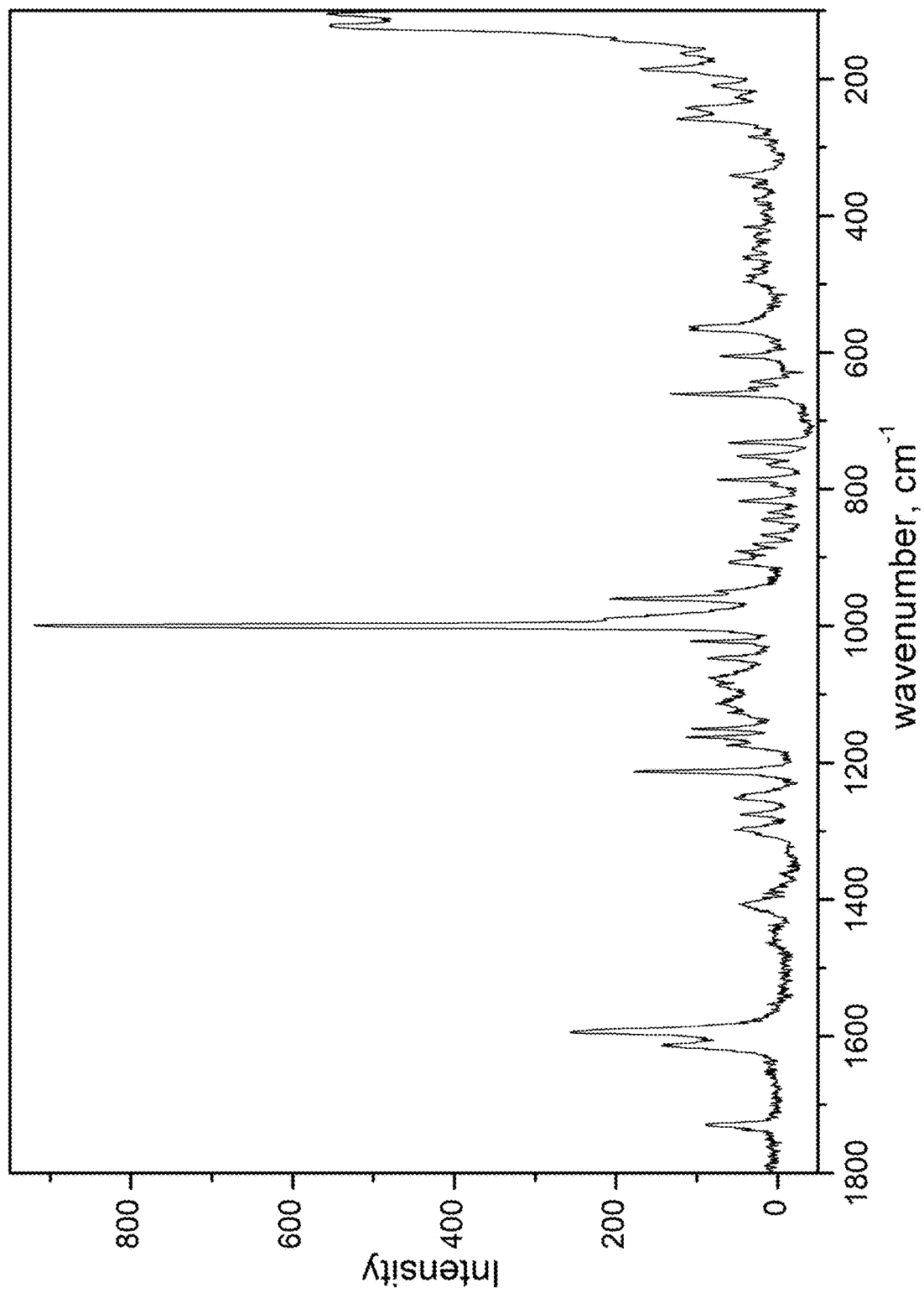
FIG. 8 is a Raman spectrum of deltamethrin Form II.

Raman spectra were recorded using a Raman microscope (DXR, Thermo Fisher Scientific, Waltham, Mass.) using a 532 nm excitation laser operating at 2 mW, with a 2 cm$^{-1}$ resolution and slit width of 50 µm; a hot stage was used when temperature control was needed. Raman spectrum for Form II is shown in FIG. 8.

Single-Crystal Structure Determination. The X-ray intensity data of Forms I and II were recorded on a Bruker D8 APEX-II CCD system using graphite-monochromated and 0.5 mm MonoCap-collimated Mo-Kα radiation (λ=0.71073 Å) with the ω scan method at 100° K.

X-ray diffraction pattern of a thin film of Form II (FIG. 9) was obtained at room temperature with Bruker D8 Discover GADDS Microdiffractometer equipped with a VANTEC-2000 two-dimensional (2D) detector and a sealed Cu X-ray tube (λ=1.54178 Å). The exposure time was 30 minutes. One-dimensional (1D) diffraction patterns were generated by integrating the 2D XRD images over the entire range of azimuthal angles spanning 5°<2θ<350 range using the XRD2EVAL program (version 2009.5-0; Bruker AXS Inc., Madison, Wis., 2009).

Example 1: Phase Behavior of Deltamethrin Polymorphs

Figures 4A, 4B, 4C:
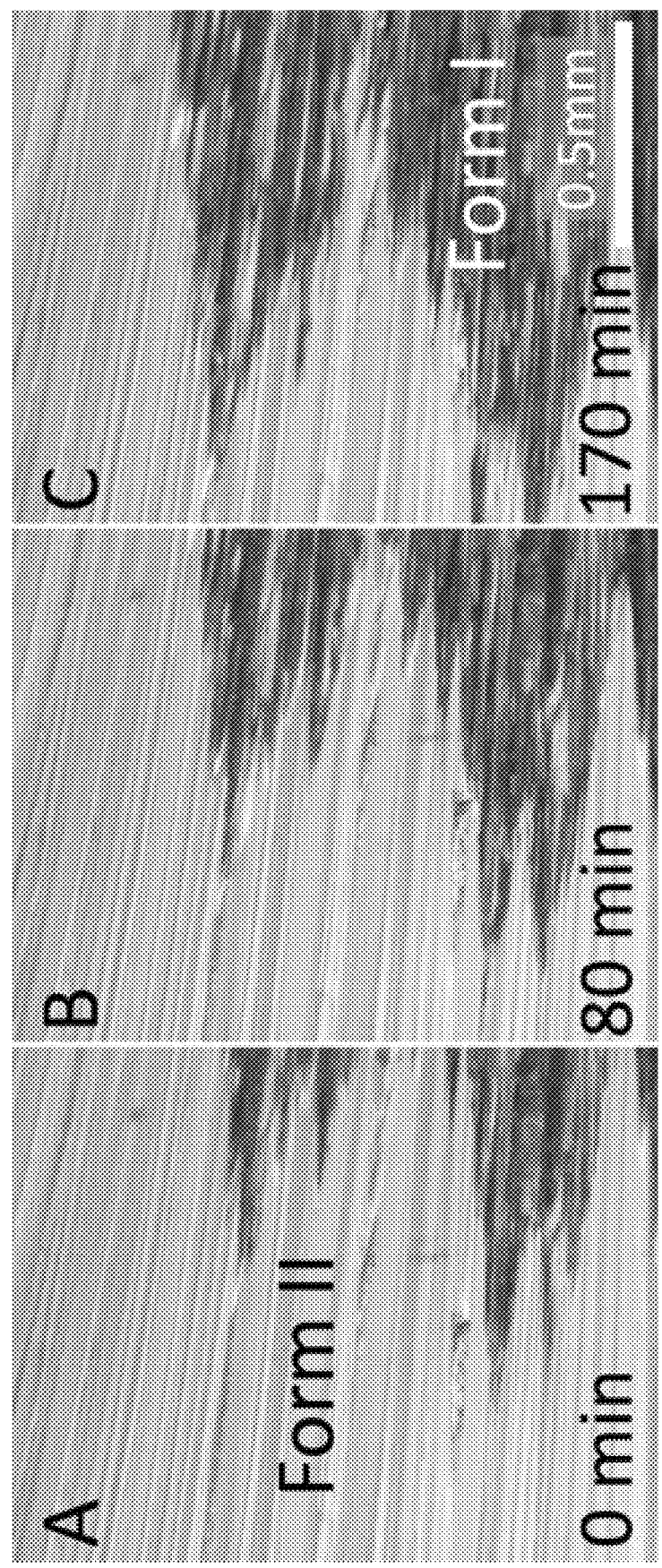
FIGS. 4A, 4B, and 4C show the transformation of deltamethrin Form II spherulite (FIG. 4A) to deltamethrin Form I (FIG. 4C) observed between crossed polarizers at room temperature.

Thermodynamic stability of deltamethrin polymorphs was evaluated by the phase transformation behaviors and respective melting points. Form II melted at 60° C., which is significantly lower than the melting point of Form I (98° C.). A crystalline film of Form II confined between glass slides did not transform to Form I after 6 months at room temperature. Rarely, transformation from Form II to Form I can be observed between crossed polarizers when spherulites of Form II are in contact with concomitant polycrystalline Form I (FIG. 4A, 4B). Form II fibers grow radially along their <010> direction. When viewed perpendicular to this direction, as shown in FIG. 4A, FIG. 4B, and FIG. 4C, the spherulites exhibit the expected birefringence due to radial orientation of the spherulite fibers. Upon phase transformation to Form I, the orientation of new grains become misaligned, resulting in a loss of observable birefringence. At room temperature the transformation can be observed by a moving growth front, which advances at a velocity of 0.3 µm/min. These observations are consistent with a room temperature stability ranking Form I> Form II.

Example 2: Preparation of Deltamethrin Powders and Deltamethrin Dusts

Powdered deltamethrin Form I was used as obtained (Sigma-Aldrich). Deltamethrin Form II was obtained by growth from the melt.

Deltamethrin Form I dust was purchased from Control Solution. Inc (trade name "D-Fense Deltamethrin Dust"). Deltamethrin Form II dust was prepared by heating Form I dust in a kitchen microwave oven (AmazonBasics Microwave, 700 W) for 100 seconds, then allowing the dust to cool to room temperature.

One of the most widely used formulations of deltamethrin is "dust," in which microcrystals of the active ingredient are diluted with 99.5% solid inert component. The dust of deltamethrin Form I comprising 0.05% deltamethrin Form I and 99.5% solid inert ingredients may be purchased from Control Solution Inc. (trade name D-Fense Deltamethrin Dust) and used without further treatment. Considering that Form II predominates when grown from melt, dust of deltamethrin containing Form I was heated in a kitchen microwave oven (700 W) for 100 seconds, then cooled to room temperature. In this way, deltamethrin Form I dust transformed into deltamethrin Form II dust. Lethality assays to confirm the transformation were used because at 0.05 weight %, direct assays of deltamethrin in dust were not possible.

Example 3: Polymorph Lethality—Dust: Fruit Flies

The effect of deltamethrin polymorphs on fruit flies was determined by the residual exposure method. Bruck, D. J.; Bolda, M.; Tanigoshi, L.; Klick, J.; Kleiber, J.; DeFrancesco, J.; Gerdeman, B.; Spitler, H. Laboratory and field comparisons of insecticides to reduce infestation of *Drosophila suzukii* in berry crops. *Pest. Manag. Sci.* 2011, 67, 1375-1385. Lethality assays were performed for each powder sample as well as a control. Female fruit flies (*Drosophila melanogaster*) were temporarily anesthetized by $CO_2$ exposure, then transferred to the 35 mm diameter petri dishes with deltamethrin dust. The dishes were covered with their mating top and the motion of the fruit flies was recorded to establish knockdown time (i.e., the time after which there was no further translational motion).

The lethalities of the two crystalline forms of deltamethrin were compared by exposing fruit flies (*Drosophila melanogaster*), a well-established model for pesticide development (Schneider, D. Using *Drosophila* as a Model Insect. *Nat. Rev. Genet.* 2000, 1, 218-226), to 2 mg of the respective dusts (containing 1 g deltamethrin Form I or Form II)

dispersed evenly in 35 mm-diameter plastic Petri dishes. Each trial was performed in triplicate for each crystalline form, as well as a control.

The motions of fruit flies were monitored by a video camera. A custom designed video process programmer was used to record the onset of hyperactivity and to track the time required for the expiration of the flies, as measured by knockdown. Form I-exposed flies began exhibiting hyperactivity at 40 minutes; no individual survived more than 210 minutes. Form II-exposed fruit flies began exhibiting hyperactivity as soon as they were exposed to the dust containing deltamethrin Form II; no individual survived more than 40 minutes. (FIG. 5A). Both the onset of hyperactivity and death occurred much later for deltamethrin Form I-exposed flies.

Lethality was deduced by the standard measurement of knockdown time, defined as time when a fly is immobile in a supine or sideways position for at least one second (i.e., no translational motion). Lindquist, A. W.; Jones, H. A.; Madden, A. H. DDT Residual-type sprays as affected by light. *J. Econ. Entomol.* 1946, 39, 55-59. Paralyzed flies never recover.

FIGS. 5A and 5B depict the graphs of the lethality comparison of the two forms of deltamethrin, in terms of fly velocities and knockdown times. The corresponding average knockdown times and median knockdown times ($KT_{50}$) are denoted. The median knockdown time ($KT_{50}$) for each polymorph was determined from multiple trials using twenty female flies each. $KT_{50}$ is defined as the time required to render 50 percent of the insects motionless. Kawada, H.; Dida, G. O.; Ohashi, K.; Komagata, O.; Kasai, S.; Tomita, T.; Sonye, G.; Maekawa, Y.; Mwatele, C.; Njenga, S. M.; Mwandawiro, C; Minakawa, N.; Takagi, M. Multimodal pyrethroid resistance in malaria vectors, *Anopheles gambiae* s.s., *Anopheles arabiensis*, and *Anopheles funestus* s.s. in Western Kenya. *PLoS One* 2011, 6, No. e22574; Limoee, M.; Ladonni, H.; Enayati, A. A.; Vatandoost, H.; Aboulhasani, M. Detection of pyrethroid resistance and cross resistance to DDT in seven field-collected strains of the German cockroach, *Blattella germanica* (L.) (*Dictyoptera: Blattellidae*). *J Biol. Sci.* 2006, 6, 382-387. The average knockdown times for 2 mg deltamethrin dusts with Form I and Form II were 123 minutes and 21 minutes, respectively. The $KT_{50}$ values were 113 minutes and 20 minutes, respectively (FIG. 5B). These results demonstrated the lethality ranking of two ambient polymorphs of deltamethrin, Form II> Form I, i.e. deltamethrin Form II is more lethal than Form I.

Example 4: Polymorph Lethality—Dust: *Aedes* Mosquitoes

The effect of deltamethrin polymorphs on yellow fever mosquitos (*Aedes aegypti*) was determined by the residual exposure method. Bruck, D. J.; Bolda, M.; Tanigoshi, L.; Klick, J.; Kleiber, J.; DeFrancesco, J.; Gerdeman, B.; Spitler, H. Laboratory and field comparisons of insecticides to reduce infestation of *Drosophila suzukii* in berry crops. *Pest. Manag. Sci.* 2011, 67, 1375-1385. Lethality assays were performed for each dust sample as well as a control. Female *Aedes* mosquitoes were temporarily anesthetized by $CO_2$ exposure, then transferred to the 90 mm diameter petri dishes with deltamethrin dust. The dishes were covered with their mating top and the motion of the mosquitoes was recorded to establish knockdown time (i.e., the time after which there was no further translational motion).

The lethalities of the two crystalline forms of deltamethrin were compared by exposing yellow fever mosquitos (*Aedes aegypti*) to 2 mg of the respective dusts (containing 1 g deltamethrin Form I or Form II) dispersed evenly in 90 mm-diameter plastic Petri dishes. Each trial was performed in duplicate for each crystalline form, as well as a control.

Figures 6A, 6B:
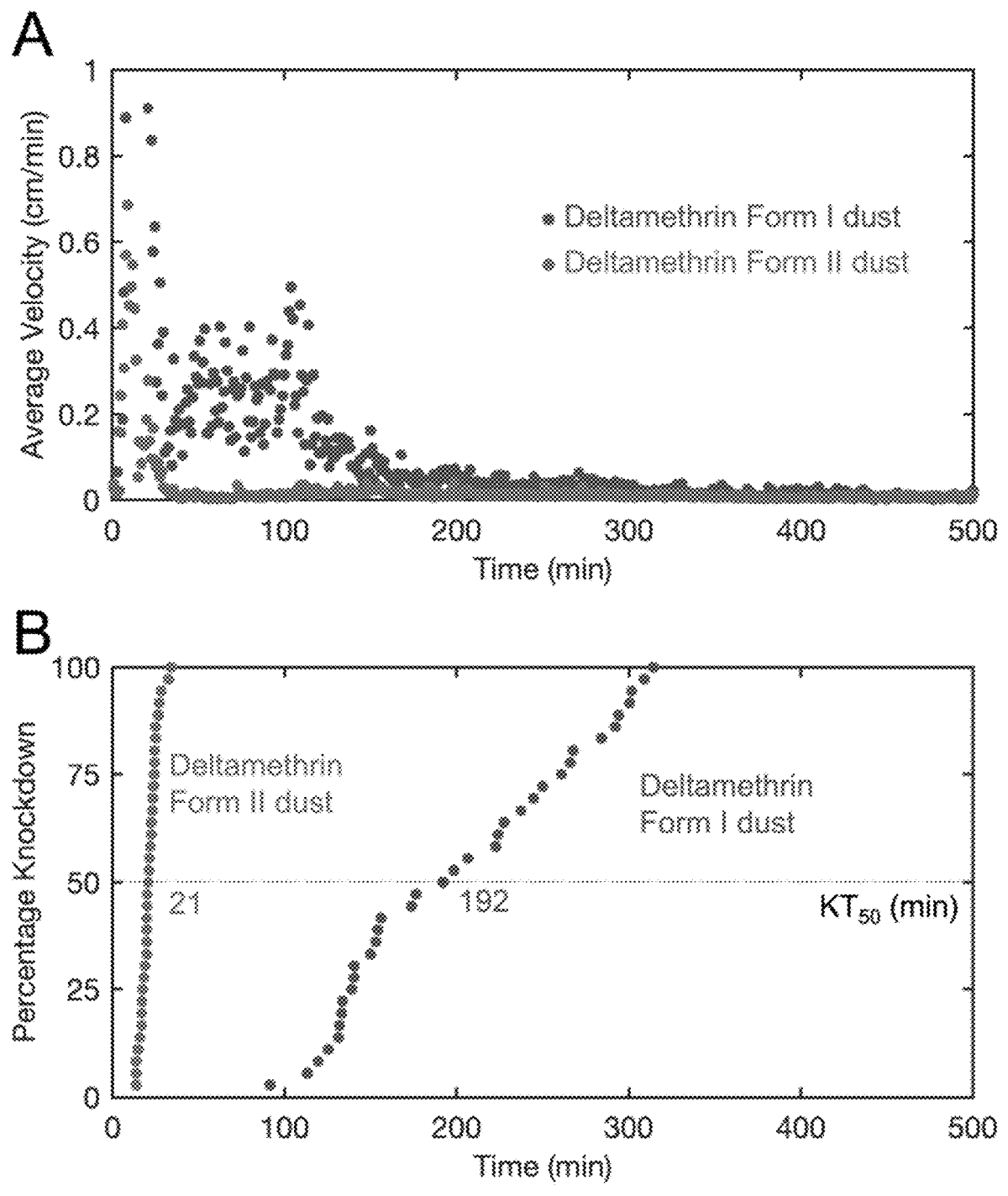

The motions of mosquitoes were monitored by a video camera. A custom designed video process programmer was used to record the onset of hyperactivity and to track the time required for the expiration of the mosquitoes, as measured by knockdown. No Form I-exposed fly survived more than 300 minutes. Form II-exposed fruit flies began exhibiting hyperactivity as soon as they were exposed to the dust containing deltamethrin Form II; no individual survived more than 30 minutes. (FIG. 6A). The death occurred much later for deltamethrin Form I-exposed mosquitoes.

Lethality was deduced by the standard measurement of knockdown time, defined as time when a mosquito is immobile in a supine or sideways position for at least one second (i.e., no translational motion). Lindquist, A. W.; Jones, H. A.; Madden, A. H. DDT Residual-type sprays as affected by light. *J. Econ. Entomol.* 1946, 39, 55-59. Paralyzed flies never recover.

FIGS. 6A and 6B depict the graphs of the lethality comparison of the two forms of deltamethrin, in terms of mosquito velocities and knockdown times. The corresponding average knockdown times and median knockdown times ($KT_{50}$) are denoted. The median knockdown time ($KT_{50}$) for each polymorph was determined from multiple trials using twenty female mosquitoes each. $KT_{50}$ is defined as the time required to render 50 percent of the insects motionless. Kawada, H.; Dida, G. O.; Ohashi, K.; Komagata, O.; Kasai, S.; Tomita, T.; Sonye, G.; Maekawa, Y.; Mwatele, C.; Njenga, S. M.; Mwandawiro, C; Minakawa, N.; Takagi, M. Multimodal pyrethroid resistance in malaria vectors, *Anopheles gambiae* s.s., *Anopheles arabiensis*, and *Anopheles funestus* s.s. in Western Kenya. *PLoS One* 2011, 6, No. e22574; Limoee, M.; Ladonni, H.; Enayati, A. A.; Vatandoost, H.; Aboulhasani, M. Detection of pyrethroid resistance and cross resistance to DDT in seven field-collected strains of the German cockroach, *Blattella germanica* (L.) (*Dictyoptera: Blattellidae*). *J. Biol. Sci.* 2006, 6, 382-387. The average knockdown times for 2 mg deltamethrin Form I and Form II dust were 202 minutes and 22 minutes, respectively. The $KT_{50}$ values were 192 minutes and 21 minutes, respectively (FIG. 6B). These results demonstrated the lethality ranking of two ambient polymorphs of deltamethrin, Form II> Form I, i.e. deltamethrin Form II is more lethal than Form I.

Example 5: Polymorph Lethality—Thin Film

The knockdown times for neat thin films are too short to allow a valid comparison of their lethality. Therefore, thin films of deltamethrin Form I and Form II were prepared and partially coated by nebulized polyethylene glycol, producing islands of inert material with a small fraction of the deltamethrin film exposed (FIG. 7B). The amount of polyethylene glycol coating was adjusted so that knockdown times could be measured on a timescale comparable to that observed for the deltamethrin dusts. The corresponding average knockdown times and median knockdown times ($KT_{50}$) are denoted. The average knockdown times for polyethylene glycol coated deltamethrin Form I and Form II crystalline film were 385 minutes and 70 minutes, respectively. The $KT_{50}$ values were 400 minutes and 61 minutes, respectively (FIG. 7B).

As shown in FIG. 7, the knockdown times for the thin films are shorter for Form II than for Form I, identical to the behavior of the corresponding deltamethrin dusts. This confirms that Form I dust is transformed to Form II dust by the microwave heating treatment.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A crystalline form of deltamethrin, which is Form II, having a thin film X-ray diffraction pattern comprising peaks at 8.3, 10.7, 16.9, 18.4, and 25.2 degrees two-theta (2θ).

2. The crystalline form of claim 1 having a Raman spectrum as shown in FIG. 8.

3. The crystalline form of claim 1 having an X-ray diffraction pattern as shown in FIG. 9.

4. The crystalline form of claim 1 comprising peaks at 8.3, 10.7, 12.5, 14.9, 16.9, 18.4, 19.7, 21.3, and 25.2 degrees two-theta (2θ).

5. The crystalline form of claim 1 having a single crystal structure determined at 100 K and refined in the space group C2, Z=4, a=20.753(4) Å, b=6.1857(12) Å, c=17.955(4) Å, β=114.654(3)°, V=2094.81 Å.

6. The crystalline form claim 1 which is isolated.

7. The crystalline form of claim 1 which is substantially free of other crystalline forms.

8. A process for preparing the crystalline form of claim 1, comprising melting deltamethrin Form I, cooling the molten deltamethrin to room temperature, and growing crystals of deltamethrin Form II from the molten deltamethrin.

9. A pesticidal composition comprising the crystalline form of claim 1.

10. The pesticidal composition of claim 9, wherein the crystalline form is present in the composition in an amount of about 0.01% to about 5% by weight.

11. The pesticidal composition of claim 9, wherein the crystalline form is present in the composition in an amount of about 0.5% by weight.

12. A method of controlling a pest comprising applying to the pest or its locus the crystalline form of claim 1.

13. The method of claim 12, wherein the pest is an insect.

14. The method of claim 13, wherein the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

15. A method of controlling a pest comprising applying to the pest or its locus the pesticidal composition of claim 9.

16. The method of claim 15, wherein the pest is an insect.

17. The method of claim 16, wherein the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

* * * * *